United States Patent
Deur-Bert et al.

(10) Patent No.: US 10,053,404 B2
(45) Date of Patent: *Aug. 21, 2018

(54) PROCESS FOR THE PREPARATION OF 2,3,3,3-TETRAFLUOROPROPENE

(71) Applicant: Arkema France, Colombes (FR)

(72) Inventors: Dominique Deur-Bert, Charly (FR); Bertrand Collier, Saint-Genis-Laval (FR); Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/095,911

(22) Filed: Apr. 11, 2016

(65) Prior Publication Data

US 2016/0221901 A1  Aug. 4, 2016

Related U.S. Application Data

(63) Continuation of application No. 14/363,918, filed as application No. PCT/IB2011/003260 on Dec. 14, 2011, now Pat. No. 9,334,208.

(51) Int. Cl.
*C07C 17/25* (2006.01)
*C07C 17/20* (2006.01)
(Continued)

(52) U.S. Cl.
CPC ............ *C07C 17/25* (2013.01); *B01J 23/26* (2013.01); *B01J 23/866* (2013.01); *B01J 27/132* (2013.01);
(Continued)

(58) Field of Classification Search
CPC .............................. C07C 17/25; C07C 17/206
See application file for complete search history.

(56) References Cited

U.S. PATENT DOCUMENTS 7,795,480 B2   9/2010  Merkel et al.
9,061,956 B2*  6/2015  Pigamo ................. C07C 17/206
(Continued)

FOREIGN PATENT DOCUMENTS

EP    2 103 587        9/2009
WO    WO 2009/003157   12/2008
(Continued)

OTHER PUBLICATIONS

International Search Report for PCT/IB2011/003260 dated Oct. 1, 2012.

*Primary Examiner* — Medhanit W Bahta
(74) *Attorney, Agent, or Firm* — NK Patent Law, PLLC

(57) ABSTRACT

The present invention provides a process for preparing 2,3,3,3-tetrafluoropropene from 1,1,1,2,3-pentachloropropane and/or 1,1,2,2,3-pentachloropropane, comprising the following steps: (a) catalytic reaction of 1,1,1,2,3-pentachloropropane and/or 1,1,2,2,3-pentachloropropane with HF into a reaction mixture comprising HCl, 2-chloro-3,3,3-trifluoropropene, 2,3,3,3-tetrafluoropropene, unreacted HF, and optionally 1,1,1,2,2-pentafluoropropane; (b) separating the reaction mixture into a first stream comprising HCl and 2,3,3,3-tetrafluoropropene and a second stream comprising HF, 2-chloro-3,3,3-trifluoropropene and optionally 1,1,1,2,2-pentafluoropropane; (c) catalytic reaction of the second stream into a reaction mixture comprising 2,3,3,3-tetrafluoropropene, HCl, unreacted 2-chloro-3,3,3-trifluoropropene, unreacted HF and optionally 1,1,1,2,2-pentafluoropropane and (d) feeding the reaction mixture of step (c) directly without separation to step (a).

13 Claims, 1 Drawing Sheet

(51) Int. Cl.
*C07C 21/18* (2006.01)
*C07C 17/383* (2006.01)
*C01B 7/19* (2006.01)
*B01J 37/12* (2006.01)
*B01J 37/24* (2006.01)
*B01J 37/26* (2006.01)
*B01J 23/26* (2006.01)
*B01J 23/86* (2006.01)
*B01J 27/132* (2006.01)
*C07C 17/38* (2006.01)

(52) U.S. Cl.
CPC ............... *B01J 37/12* (2013.01); *B01J 37/24* (2013.01); *B01J 37/26* (2013.01); *C01B 7/191* (2013.01); *C07C 17/206* (2013.01); *C07C 17/383* (2013.01); *C07C 17/38* (2013.01)

(56) References Cited

U.S. PATENT DOCUMENTS

| | | | |
|---|---|---|---|
| 9,334,208 B2 * | 5/2016 | Deur-Bert | C07C 17/206 |
| 2007/0197842 A1 | 8/2007 | Mukhopadhyay et al. | |
| 2011/0160497 A1 | 6/2011 | Deur-Bert et al. | |
| 2012/0330073 A1 * | 12/2012 | Karube | C07C 17/21 |
| | | | 570/156 |
| 2013/0267740 A1 | 10/2013 | Wendlinger et al. | |
| 2014/0031597 A1 * | 1/2014 | Deur-Bert | C07C 17/206 |
| | | | 570/160 |

FOREIGN PATENT DOCUMENTS

| | | | | |
|---|---|---|---|---|
| WO | WO 2010/123154 | 10/2010 | | |
| WO | WO 2011/135395 | 11/2011 | | |
| WO | WO 2012098420 A1 * | 7/2012 | ........... | C07C 17/206 |

* cited by examiner

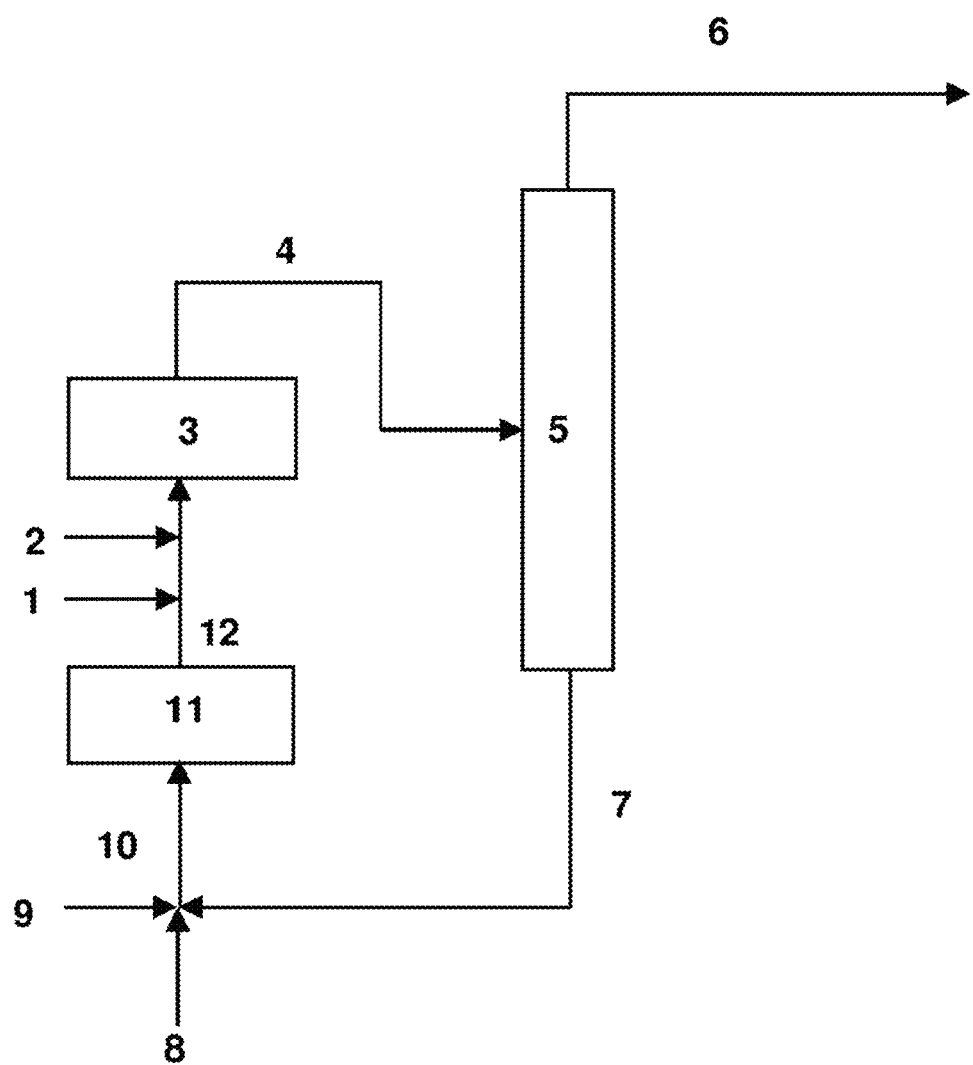

PROCESS FOR THE PREPARATION OF 2,3,3,3-TETRAFLUOROPROPENE

CROSS-REFERENCE TO RELATED APPLICATIONS

This application is a Continuation of U.S. patent application Ser. No. 14/363,918 filed Oct. 30, 2014, now allowed; which is a National Stage application of International Application No. PCT/IB2011/003260 filed Dec. 14, 2011.

FIELD OF THE INVENTION

The present invention relates to the preparation of 2,3,3,3-tetrafluoropropene (HFO-1234yf). More particularly, the present invention relates to a two reaction step process wherein pentachloropropane, including 1,1,1,2,3-pentachloropropane (HCC-240db) and/or 1,1,2,2,3-pentachloropropane (HCC-240aa), is first contacted with hydrogen fluoride (HF), this first step (a) providing 2-chloro-3,3,3-trifluoropropene (HCFO-1233xf), which after separation is then converted into HFO-1234yf in a second reaction step (c).

The desired product, HFO-1234yf is known to have utility as a foam blowing agent, refrigerant, aerosol propellant, heat transfer media, fire extinguisher, etc. Furthermore, HFO-1234yf is known to have zero Ozone Depletion Potential (ODP) and very low Global Warming Potential (GWP) of much less than 150.

TECHNICAL BACKGROUND

The protocol of Montreal for the protection of the ozone layer led to the end of the use of chlorofluorocarbons (CFCs). Less aggressive compounds for the ozone layer, such as the hydrofluorocarbons (HFCs) e.g. HFC-134a replaced chlorofluorocarbons. These latter compounds were indeed shown to provide greenhouse gases. There exists a need for the development of technologies, which present a low ODP (ozone depletion potential) and a low GWP (global warming potential). Although the hydrofluorocarbons (HFCs), which are compounds which do not affect the ozone layer, were identified as interesting candidates, they exhibit a relatively high GWP value. There still exists the need to find compounds which exhibit a low GWP value. Hydrofluoroolefins (HFO) were identified as being possible alternatives with very low ODP and GWP values.

Several processes of production HFOs compounds, in particular of propenes, were developed. US2009/0240090 discloses the gas-phase reaction of 1,1,1,2,3-pentachloropropane (HCC-240db) into product 2-chloro-3,3,3-trifluoropropene (HCFO-1233xf). Example 3 uses a catalyst comprised of fluorinated $Cr_2O_3$. The product HCFO-1233xf thus produced is then converted into product 2-chloro-1,1,1,2-tetrafluoropropane (HCFC-244bb) in a liquid phase reaction. This product HCFC-244bb is then converted into the desired HFO-1234yf. This process comprises three reaction steps.

WO2005/108334, example 3, discloses that HCC-240db is passed through a flow reactor for a contact time for about 5 to 50 seconds at about 250-400° C. in the presence of 5 molar excess of HF over a 50 g ⅛-inch $Cr_2O_3$ catalyst bed to give HCFC-244db (2-chloro-1,1,1,3-tetrafluoropropane). It is further indicated that the HCFC-244db is then dehydrochlorinated by passing it over a $Cr_2O_3$ catalyst (50 g) at 425-550° C. with a contact time of 25 to 30 seconds to afford product HFO-1234ze (1,3,3,3-tetrafluoropropene).

The literature is generally about a scheme involving preparation of HFO-1234yf via the HCFC-244 route.

There is still a need for further processes for manufacturing HFO-1234yf.

SUMMARY OF THE INVENTION

The invention is based on the finding that it is possible to prepare the compound HFO-1234yf starting from pentachloropropane. The process according to the present invention includes two reaction steps with a separation step in between.

The present invention is advantageous over processes described in prior art in that the process includes the ability to maximize raw material utilization and product yields for a long time. It is also characterised by the ability to handle and recover by-products that are commercially valuable. Moreover, the process is conducted without preparing in an intermediate stage the product HCFC-244bb (2-chloro-1,1,1,2-tetrafluoropropane).

Hence, the invention provides a process for preparing 2,3,3,3-tetrafluoropropene from 1,1,1,2,3-pentachloropropane and/or 1,1,2,2,3-pentachloropropane, comprising the following steps:

(a) catalytic reaction of 1,1,1,2,3-pentachloropropane and/or 1,1,2,2,3-pentachloropropane with HF into a reaction mixture comprising HCl, 2-chloro-3,3,3-trifluoropropene, 2,3,3,3-tetrafluoropropene, unreacted HF, and optionally 1,1,1,2,2-pentafluoropropane;

(b) separating the reaction mixture into a first stream comprising HCl and 2,3,3,3-tetrafluoropropene and a second stream comprising HF, 2-chloro-3,3,3-trifluoropropene and optionally 1,1,1,2,2-pentafluoropropane;

(c) catalytic reaction of the second stream into a reaction mixture comprising 2,3,3,3-tetrafluoropropene, HCl, unreacted 2-chloro-3,3,3-trifluoropropene, unreacted HF and optionally 1,1,1,2,2-pentafluoropropane and (d) feeding the reaction mixture of step (c) directly to step (a) without separation.

The term "Organics" is defined herein as any compound comprising carbon atom, hydrogen atom and chlorine atom and/or fluorine atom such as 1,1,1,2,3-pentachloropropane, 1,1,2,2,3-pentachloropropane, 1,1,1,2,2-pentafluoropropane and 2-chloro-3,3,3-trifluoropropene.

Embodiments are the following:

step (a) and/or step (c) is carried out in a gas-phase.

the process is carried out in presence of oxygen or chlorine.

The molar ratio of oxygen with respect to Organics in step (a) is 0.005 to 2, preferably 0.01 to 1.5.

The molar ratio of oxygen with respect to Organics in step (c) is 0.005 to 2, preferably 0.01 to 1.5.

step (a) and/or step (c) is carried out in a gas-phase in the presence of a chromium based catalyst.

the 1,1,1,2,3-pentachloropropane contains up to 40 mol % of isomer 1,1,2,2,3-pentachloropropane.

the process is continuous.

Step (a) and/or step (c) is carried out at a pressure from 0.1 to 50 bar absolute, preferably from 0.3 to 15 bar absolute.

Step (a) and/or step (c) is carried out at a temperature of from 100 to 500° C., preferably from 200 to 450° C.

Step (a) and/or step (c) is or are carried out at a molar ratio HF:Organics from 4:1 to 100:1, preferably 5:1 to 50:1.

Contact time in step (a) is between 1 and 50 s, preferably between 2 and 40 s.

Contact time in step (c) is between 1 and 100 s and preferably between 5 and 50 s.

BRIEF DESCRIPTION OF THE DRAWING

The FIG. is a schematic representation of a process.

DETAILED DESCRIPTION OF EMBODIMENTS

The present invention relates to a process for manufacturing 2,3,3,3-tetrafluoropropene from 1,1,1,2,3-pentachloropropane and/or 1,1,2,2,3-pentachloropropane. The process generally comprises two separate reaction steps. In the first step (a), a raw material comprising 1,1,1,2,3-pentachloropropane and/or 1,1,2,2,3-pentachloropropane reacts, in the presence of a catalyst, with an excess of anhydrous HF, preferably in a vapor phase, to produce a mixture of HCl, 2-chloro-3,3,3-trifluoropropene, 2,3,3,3-tetrafluoropropene. The first reaction step can be performed in a single reactor. The effluent stream exiting the reactor may optionally comprise additional components such as 1,1,1,2,2-pentafluoropropane (HFC-245cb) and unreacted HF.

The product stream of the first step (a) is then sent to a separation step (b), preferably distillation, to give a first stream comprising HCl and HFO-1234yf and a second stream comprising HF, 2-chloro-3,3,3-trifluoropropene and optionally 1,1,1,2,2-pentafluoropropane. The second stream is then fed in a second reactor optionally with fresh HF in conditions sufficient to give a product stream comprising HFO-1234yf, HFC-245cb, together with unreacted HCFO-1233xf and HF. This product stream is sent directly to step (a).

Step (a)

Step (a) of the present process involves contacting fresh HCC-240db and/or HCC-240aa and the reaction products from step (c) with HF in the reaction zone in the presence of a catalyst, preferably in the gas phase, under conditions sufficient to give fluorination products comprising mainly HCFO-1233xf and HFO-1234yf.

Typically, the step (a) is carried out with a molar ratio HF:Organics from 4:1 to 100:1, preferably 5:1 to 50:1.

Typically, the process of the invention is carried out at a pressure from 0.1 to 50 bar absolute, preferably 0.3 to 15 bar absolute.

Typically, the process of the invention is carried out at a temperature of from 100 to 500° C., preferably from 200 to 450° C.

Contact times (catalyst volume divided by the total flow rate of reactants and co-feeds, adjusted to the operating pressure and temperature) are typically from 1 to 50 sec, preferably from 2 to 40 sec.

An oxygen co-feed may be used to extend the catalyst lifetime, typically the molar ratio of oxygen/Organics is from 0.005 to 2, preferably 0.01 to 1.5.

The oxygen can be introduced as an oxygen-containing gas such as air, pure oxygen, or an oxygen/nitrogen mixture.

A chlorine cofeed may also be used instead of the oxygen cofeed (with the same operating conditions).

Chlorine can be introduced as a chlorine-containing gas such as pure chlorine, or a chlorine/nitrogen mixture.

Catalyst

The catalyst is for example a catalyst based on a metal including a transition metal oxide or a derivative or halide or oxyhalide such a metal. Catalysts are e.g. $FeCl_3$, chromium oxyfluoride, chromium oxides (that can optionally be subject to fluorination treatments), chromium fluorides, and mixtures thereof. Other possible catalysts are the catalysts supported on carbon, catalysts based on antimony, catalysts based on aluminum (as $AlF_3$ and $Al_2O_3$ and oxyfluoride of alumina and aluminum fluoride). Generally speaking, catalysts that can be used are chromium oxyfluoride, aluminium fluoride and oxyfluoride, and supported or unsupported catalyst containing a metal such as Cr, Ni, Fe, Zn, Ti, V, Zr, Mo, Ge, Sn, Pb, Mg, Sb. Reference can also be made to the disclosures of WO-A-2007/079431, at page 7, lines 1-5 and 28-32, EP-A-939071, at paragraph [0022], WO2008/054781 at page 9 line 22 to page 10 line 34, WO2008/040969 in claim 1, all incorporated herein by reference.

Prior to its use, the catalyst is subjected to activation with air, oxygen or chlorine and/or with HF.

Prior to its use, the catalyst is preferably subjected to an activation process with oxygen or air and HF at a temperature of 100-500° C., preferably from 250-500° C. and more preferably from 300-400° C. The period of activation is preferably from 1 to 200 h and more preferably form 1 to 50 h.

This activation can be followed by a final fluorination activation step in the presence of an oxidizing agent, HF and Organics. The molar ratio of HF/Organics is preferably from 2 to 40 and the molar ratio of oxidizing agent/Organics is preferably from 0.04 to 25. The temperature of final activation is preferably from 300 to 400° C. and more preferably for about 6 to 100 h.

The catalyst is preferably a chromium based catalyst and more preferably a mixed catalyst comprising chromium.

A preferred embodiment uses a particular catalyst, which is a mixed catalyst, containing both chromium and nickel. The molar ratio Cr:Ni, with respect to the metallic element is generally between 0.5 and 5, for example between 0.7 and 2, including close to 1. The catalyst may contain in weight from 0.5 to 20% chromium and 0.5 to 20% nickel, preferably between 2 and 10% of each metal.

The metal may be present in metallic form or as derivatives, including oxide, halide or oxyhalide. These derivatives, including halide and halide oxides, are obtained by activation of the catalytic metal. Although the activation of the metal is not necessary, it is preferred.

The support is preferably made from aluminum. There are several possible carriers such as alumina, activated alumina or aluminum derivatives. These derivatives include aluminum halides and halide oxides of aluminum, for example described in U.S. Pat. No. 4,902,838, or obtained by the activation process described below.

The catalyst may include chromium and nickel in a non-activated or activated form, on a support that has been subjected to activation or not.

Reference can be made to WO2009/118628, and especially to the disclosure of the catalyst from page 4, line 30 to page 7, line 16, which is incorporated herein by reference.

Another preferred embodiment uses a mixed catalyst containing chromium and at least an element chosen from Mg and Zn. The atomic ratio of Mg or Zn/Cr is preferably from 0.01 and 5.

Step (b)

The product stream of step(a) comprising HCl, 2-chloro-3,3,3-trifluoropropene, 2,3,3,3-tetrafluoropropene, unreacted HF, and optionally 1,1,1,2,2-pentafluoropropane enters a separation unit, for example a distillation column, to give a first stream comprising HCl and 2,3,3,3-tetrafluoropropene and a second stream comprising HF, 2-chloro-3,3, 3-trifluoropropene and optionally 1,1,1,2,2-pentafluoropropane. Step (b) can be performed at a temperature preferably from −90 to 150° C. and more preferably from −85 to 100°

C., and at a pressure preferably from 0.1 to 50 bar abs and more preferably from 0.3 to 5 bar abs.

The first stream leaves the reaction system and enters an acid production unit to produce hydrochloric acid and HFO-1234yf.

HFO-1234yf and intermediate products are readily recovered by any means known in the art, such as by scrubbing, washing, extraction, decantation and preferably distillation. Any stream can also be further purified by distillation techniques.

Step (c)

Step (c) of the present invention is a fluorination reaction, preferably gas phase, of the second stream of step (b) with HF in the presence of a catalyst and it comprises mainly fluorination of 2-chloro-3,3,3-trifluoro-1-propene obtained in step (a) in 2,3,3,3-tetrafluoro-1-propene, the desired product.

Step (c) can be carried out in a single or multiple gas-phase reactor.

This step of the process of the present invention, as well as the entire process, is preferably run continuously.

This step involves mainly contacting HCFO-1233xf with HF in the reaction zone in a gas phase, under conditions sufficient to convert the HCFO-1233xf to fluorination products comprising HFO-1234yf and HFC-245cb. Such conditions are given below. In addition to the fluorinated products, unreacted HCFO-1233xf, unreacted HF and other co-produced underfluorinated intermediates which may be present in minor amounts are sent directly to step (a).

Typically, this step is carried out with a molar ratio HF:Organics from 4:1 to 100:1, more preferably 5:1 to 50:1.

Typically, this step is carried out at a pressure from 0.1 to 50 bars, preferably 0.3 to 15 bars absolute.

Typically, this step is carried out at a temperature of from 100 to 500° C., preferably from 200 to 450° C.

Contact times (catalyst volume divided by the total flow rate of reactants and co-feeds, adjusted to the operating pressure and temperature) are typically from 1 to 100 sec, preferably from 5 to 50 sec.

An oxygen co-feed may be used to extend the catalyst lifetime, typically the molar ratio of oxygen/Organics is from 0.005 to 2, preferably 0.01 to 1.5.

The oxygen can be introduced as an oxygen-containing gas such as air, pure oxygen, or an oxygen/nitrogen mixture.

A chlorine cofeed may also be used in lieu of the oxygen cofeed (with the same operating conditions).

Chlorine can be introduced as a chlorine-containing gas such as pure chlorine, or a chlorine/nitrogen mixture.

The catalyst described above can be used in this step. It can be similar to the one used in step (a) or different.

Reaction steps (a) and (c) are implemented in a dedicated reactor for reactions involving halogens. Such reactors are known to those skilled in the art and can include linings based eg Hastelloy®, Inconel®, Monel® or fluoropolymers. The reactor may also include means of heat exchange, if necessary.

Besides advantages described above, the reaction step © which is a critical step can be performed in the absence of the huge amount of HCl generated in the first step and also in some embodiment such as when the reactor of step (c) is placed above that of the reactor of step (a), loading and unloading of the catalyst is easier. Moreover, since unreacted HCFO-1233xf coming from step (c) also reacts in step(a), the yield of HFO-1234yf based on pentachloropropane is higher.

The present invention can be practised in a compact plant since only one separation cycle is needed and is also low energy consuming.

The FIG. represents the process carried out in one embodiment of the invention. The first gas-phase reactor (3) is fed with fresh HCC-240db (2) and optionally fresh HF (1). The reaction mixture (4) exiting the reactor comprises HCl, HCFO-1233xf, unreacted HF, HFO-1234yf and optionally HFC-245cb. This reaction stream is separated by distillation (5) into a first stream (6) comprising HCl, HFO-1234yf optionally with small amount of HF and minor amounts of HFC-245cb and HFO-1233xf. A second, heavier, stream (7) is obtained at the bottom of the distillation column, and comprises HF, HCFO-1233xf, HFC-245cb. HFO-1234yf can be separated and purified from stream (6) using appropriate known methods.

The second reactor (11) is fed by stream (10) which is consists of the second stream (7), optionally with fresh HF (8)and oxygen (9). The reaction mixture (12) exiting the reactor comprises HCl, unreacted HCFO-1233xf, unreacted HF, HFO-1234yf, HFC-245cb. This reaction is sent directly to the first reactor without being subjected to any separation.

The invention claimed is:

1. A process for producing 2,3,3,3-tetrafluoropropene, comprising:
    (a) reacting 1,1,1,2,3-pentachloropropane and/or 1,1,2,2,3-pentachloropropane with HF in the presence of a catalyst to produce a first reaction mixture comprising HCl, 2-chloro-3,3,3-trifluoropropene, 2,3,3,3-tetrafluoropropene, unreacted HF and optionally 1,1,1,2,2-pentafluoropropane, wherein the catalyst comprises a supported or unsupported catalyst containing at least one metal selected from the group consisting of Cr, Ni, Fe, Zn, Ti, V, Zr, Mo, Ge, Sn, Pb, Mg, Sb, Co, Ru, Rh, Pd, Os, Ir, Pt, Mn, Re, Sc, Y, La, Hf, Cu, Ag, Au, and metals having an atomic number of 58 through 71;
    (b) separating the first reaction mixture into a first stream and a second stream comprising 2-chloro-3,3,3-trifluoropropene;
    (c) reacting HF and the second stream in the presence of a catalyst to produce a second reaction mixture comprising 2,3,3,3-tetrafluoropropene, HCl, unreacted 2-chloro-3,3,3-trifluoropropene and HF and optionally 1,1,1,2,2-pentafluoropropane, wherein the catalyst comprises a supported or unsupported catalyst containing at least one metal selected from the group consisting of Cr, Ni, Fe, Zn, Ti, V, Zr, Mo, Ge, Sn, Pb, Mg, Sb, Co, Ru, Rh, Pd, Os, Ir, Pt, Mn, Re, Sc, Y, La, Hf, Cu, Ag, Au, and metals having an atomic number of 58 through 71; and
    (d) feeding the second reaction mixture of step (c) directly to step (a).

2. The process of claim 1, wherein the catalyst of step (a) is the same as the catalyst of step (c).

3. The process of claim 1, wherein step (a) and step (c) are carried out in the gas phase.

4. The process of claim 1, wherein the catalyst in step (a) and/or step (c) is a chromium based catalyst.

5. The process of claim 4, wherein the catalyst is a mixed catalyst.

6. The process of claim 4, wherein the catalyst is a supported catalyst.

7. The process of claim 1, wherein step (a) and/or step (c) is carried out in the presence of oxygen or chlorine.

8. The process of claim 1, wherein step (a) and/or step (c) is carried out at a temperature of 100 to 500° C.

9. The process of claim 1, wherein step (a) and/or step (c) is carried out at a molar ratio of HF:organic feed from 4:1 to 100:1.

10. The process of claim 1, wherein the molar ratio of oxygen:organic feed in step (a) and/ or step (c) is 0.005 to 2.

11. The process of claim 1, further comprising separating HCl from the reaction mixture after step (a).

12. The process of claim 1, wherein the reactor of step (c) is placed above the reactor of step (a).

13. The process of claim 1, wherein the catalyst of any of step (a) or step (c) comprises one or more of chromium oxide, chromium oxyfluoride, chromium fluoride, aluminum fluoride, or aluminum oxyfluoride.

\* \* \* \* \*